United States Patent [19]

Cherkofsky

[11] B 4,000,196
[45] Dec. 28, 1976

[54] 1,1,3-TRISUBSTITUTED HYDROXYGUANIDINES

[75] Inventor: Saul Carl Cherkofsky, Wilmington, Del.

[73] Assignee: E. I. Du Pont de Nemours and Company, Wilmington, Del.

[22] Filed: Dec. 17, 1974

[21] Appl. No.: 533,652

[44] Published under the second Trial Voluntary Protest Program on March 23, 1976 as document No. B 533,652.

Related U.S. Application Data

[63] Continuation-in-part of Ser. No. 373,147, June 25, 1973, Pat. No. 3,867,447.

[52] U.S. Cl. .................. 260/565; 260/556 AR; 260/556 B; 260/556 S; 260/558 S; 260/397.7 R; 260/558 A; 260/559 T; 260/559 S; 260/559 A
[51] Int. Cl.² .................................... C07C 133/10
[58] Field of Search .......... 260/564 G, 564 A, 565, 260/556 AR, 556 B, 556 S, 558 S, 558 A, 559 T, 559 S, 559 A, 397.7

[56] References Cited

OTHER PUBLICATIONS

German Offenlegungsschrift, 2,040,628 (2/24/72).
Belzecki et al., Bull. Acad. Polo. Des Sciences, vol. 18, pp. 569–572 (1970).
Belzecki et al., J. Chem. Soc. Chem. Comm., pp. 806–807 (1970).
Braun et al., Ber. vol. 36, pp. 3660–3663 (1903).

Primary Examiner—Gerald A. Schwartz
Attorney, Agent, or Firm—Anthony P. Mentis

[57] ABSTRACT

Certain 1,1,3-trisubstituted hydroxyguanidines are useful intermediates in the preparation of 2-hydroxyguanidine O-carbamates which are antihypertensive agents. The intermediates are additionally useful as metal chelating agents and as antidepressant agents. Exemplary is 1-phenyl-1,3-dimethyl-2-hydroxyguanidine.

5 Claims, No Drawings

1,1,3-TRISUBSTITUTED HYDROXYGUANIDINES

RELATED APPLICATION

This application is a continuation-in-part of my co-pending application Ser. No. 373,147, filed June 25, 1973 now U.S. Pat. No. 3,867,447.

BACKGROUND OF THE INVENTION

Certain 1,1,3-trisubstituted hydroxyguanidines are useful intermediates in the preparation of 2-hydroxyguanidine O-carbamates which are antihypertensive agents in warm-blooded animals. The intermediates are additionally useful as metal chelating agents and as antidepressant agents in warm-blooded animals.

PRIOR ART

J. V. Braun and R. Schwarz, Ber., 36, 3660 (1903) describe the preparation of the disubstituted hydroxyguanidines:

$$R_1R_2N\overset{NOH}{\underset{}{C}}-NH_2$$

where $R_1 = \phi$; $R_2 = CH_3$; $R_1 = R_2 = $ n-propyl; and $R_1 = R_2 = \phi$.

C. Belzecki et al., J. Chem. Soc., Chem. Comm. 806, (1970) disclose that reaction of hydroxylamine with disubstituted cyanamides yields 1,1-disubstituted-2-hydroxyguanidines (I) or N,N-disubstituted-1-aminohydroxyformamidine (II);

$$\underset{R}{\overset{R}{>}}N-\underset{\underset{NOH}{|}}{C}-NH_2 \qquad R-\underset{\underset{R}{|}}{N}-\underset{\underset{ONH_2}{|}}{C}=NH$$

(I)       (II)

depending on the solvent and the cyanamide substituents.

German Offenlegungsschrift No. 2,040,628 published Feb. 24, 1972 discloses different trisubstituted hydroxyguanidines as herbicides.

SUMMARY OF THE INVENTION

The invention is a compound of the formula:

$$\text{I} \quad \underset{R^2}{\overset{R^1}{>}}N-\overset{NOH}{\underset{}{C}}-N\underset{R^3}{\overset{H}{<}} \quad \text{wherein}$$

$R^1$ is

[structure: substituted phenyl with $(CH_2)_m$ and $X_n$] in which

X is F, Cl, Br, $C_1$-$C_3$ alkyl, $C_1$-$C_3$ alkoxy, $-NO_2$, $-CF_3$, $R^4R^5NCO-$, $R^4R^5NSO_2-$, or $R^6SO_2-$;

$m$ and $n$ independently are 0 to 2;

$R^4$ and $R^5$ independently are H or $C_1$-$C_4$ alkyl;

$R^6$ is $CF_3$ or $C_1$-$C_4$ alkyl; and $R^2$ and $R^3$ independently are methyl or ethyl.

The compounds may be prepared by two methods. The reaction in method A is:

$$A. \quad R^1R^2NH + R^3-N=C=S \longrightarrow R^1R^2N\overset{S}{\underset{}{C}}NHR^3 \longrightarrow$$

II $$R^1R^2N\overset{SCH_3}{\underset{}{C}}=NR^3 \xrightarrow{NH_2OH} R^1R^2N\overset{NOH}{\underset{}{C}}NHR^3$$

III       I

In this method the thiourea II is made by reaction of a secondary amine with an isothiocyanate in an inert solvent such as ether, methylene chloride, chloroform or the like at temperatures between 0° and the solvent's boiling point for 4–12 hours. After evaporation and recrystallization or distillation, the thiourea is alkylated with methyl iodide in refluxing ethanol or with dimethyl sulfate in water at 0° for 1–4 hours. The salts are neutralized with an equivalent of base. The resultant S-methyl isothiourea III is either distilled or recrystallized. Reaction of the isothiourea compound III and hydroxylamine is carried out in methanol at 0° for 1–12 hours. The resultant product I is purified, preferably by high pressure liquid chromatography.

The reaction in method B is as follows:

$$B. \quad R^1R^2NCNHR^3 + COCl_2 \xrightarrow{\text{solvent}} \left[ R^1R^2N-\overset{Cl}{\underset{}{C}}-NHR^3 \right]^{\oplus} Cl^{\ominus}+CO_2$$

IV       V $$\left[ R^1R^2\underline{N}-\overset{Cl}{\underset{}{C}}-NHR^3 \right]^{\oplus} + H_2NOR^7 \xrightarrow[\text{acid acceptor}]{\text{solvent}} R^1R^2N-\overset{NOR^7}{\underset{}{C}}-NHR^3$$

V       VI       VII $$R^1R^2N\overset{NOR^7}{\underset{}{C}}NHR^3 \xrightarrow{\text{hydrolysis}} R^1R^2N\overset{NOH}{\underset{}{C}}NHR^3 + R^7OH$$

VII       I

In reaction method B, $R^1$, $R^2$, $R^3$ are as previously defined and $R^7$ is or SiR$_3^8$ where R$^8$ is alkyl of 1–4 carbons, including isobutyl. The substituted urea IV is reacted at −45 to 35°C. for 4–24 hours with phosgene in an inert solvent such as dimethylformamide, toluene, acetonitrile, chloroform or the like to form a chloroformamidine salt V which is then reacted at the same temperatures as above with an amine ether VI. The resulting ether compound VII is then hydrolyzed in the presence of an acid acceptor such as a tertiary amine to produce the compound I.

SPECIFIC EMBODIMENTS OF THE INVENTION

In the following illustrative examples all parts are by weight and all temperatures are centigrade unless stated otherwise.

EXAMPLE 1

1-Benzyl-1,3-dimethyl-2-hydroxyguanidine
R$^1$ = benzyl
R$^2$=R$^3$ = methyl

A 100 ml. solution of hydroxylamine generated from hydroxylamine hydrochloride (5.86 g., 0.088 mol) and potassium hydroxide (4.59 g., 0.088 mol) was cooled to 0°. To this was added a 25 ml. methanol solution of S-methyl-N-benzyl-N,N'-dimethylisothiourea (3.53 g., 0.017 mol) over a 10 minute period. The mixture was allowed to stir for 4 hours. Methanol was then removed by evaporation and the residue redissolved in methylene chloride. After two washes with 100 ml. quantities of water, the organic layer was extracted with 20 ml. 1N hydrochloric acid. The aqueous layer was then made basic to pH 9 and extracted with methylene chloride. The organic layer was dried, evaporated, and resulted in 0.100 g. of an oil. The oil was separated into its components using high pressure liquid chromatography and 40 mg. (1.2% yield) of pure 1-benzyl-1,3-dimethyl-2-hydroxyguanidine was isolated. It had thin layer chromatographic and NMR properties identical to those of an authentic sample.

EXAMPLE 2

1-Phenyl-1,3-dimethyl-2-hydroxyguanidine
R$^1$ = phenyl
R$^2$=R$^3$ = methyl

A. An 8.2 g. (0.05 mol) portion of 1-phenyl-1,3-dimethyl urea was dissolved in 100 ml. dry toluene. The solution was cooled to −22° followed by the addition of 4.9 g. (0.05 mol) liquid phosgene. The mixture was stirred for 24 hours during which time it warmed to 25°. The chloroformamidine salt

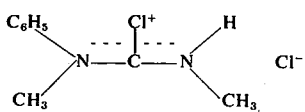

was formed as a solid. The toluene was removed by gentle decantation under nitrogen. The salt was dissolved in 50 ml. dry acetonitrile, transferred to a dropping funnel via syringe and added dropwise to a cold (−22°) 50 ml. solution of 5.85 g. (0.05 mol) 0-(2-tetrahydropyranyl) hydroxylamine and 10.1 g. (0.10 mol) triethylamine. After addition, the reaction mixture was warmed to 25° and stirred for 2 hrs. It was then poured into 100 ml. methylene chloride. The methylene chloride layer was extracted six times with 100 ml. portions of water, dried, and the solvent removed. The resultant liquid was dissolved in 55 ml. 1N HCl, 100 ml. water, and heated on a steam bath for 1 hr. The aqueous phase was extracted with two 100 ml. portions of methylene chloride, then made basic with 60 ml. 1N NaOH and extracted with two 100 ml. portions of methylene chloride. The organic layer was dried (MgSO$_4$) and evaporated to give 4.3 g. (48%) of 1-phenyl-1,3-dimethylhydroxyguanidine as a viscous liquid: NMR: (CDCl$_3$) δ 2.47 (S, 3H), δ 3.15 (S, 3H), δ 6.43- 7.40 (m, 6H). Mass Spectrum; Calc'd for C$_9$H$_{13}$N$_3$O: 179.1058. Found: 179.1041. HCl Salt: mp, 164°–168°. Analysis of HCl Salt: Calc'd for C$_9$H$_{14}$ClN$_3$O:C, 50.23; H, 6.51; N, 19.53 Found: C, 50.96; H, 6.51; N, 18.33

B. The above compound is also made by the reaction of S-methyl-N-phenyl-N,N'-dimethylisothiourea (3.3g, 0.017 mol) with hydroxylamine (0.088 mol) generated from hydroxylamine hydrochloride (5.86g, 0.088 mol) as in Example 1. The compound was confirmed by comparison of its NMR and thin layer chromatographic R$_f$ values with a previously prepared compound. The yield was calculated to be about 1%.

EXAMPLE 3

1-Phenyl-1-methyl-3-ethyl-2-hydroxyguanidine
R$^1$ = phenyl
R$^2$ = methyl
R$^3$ = ethyl The procedure of Example 2 was repeated but using 8.9 g. (0.05 mol) of 1-phenyl-1-methyl-3-ethylurea. Thin layer chromatography showed the presence of unreacted starting urea and 0-(2-tetrahydropyranyl hydroxylamine). The crude product amounted to 6.3 g. but the physical properties after purification indicated that the 1-phenyl-1-methyl-3-ethylhydroxyguanidine was pure: NMR (CDCl$_3$) 6, (0.98, t J=7Hz, 3H); δ, (2.86 q, j=7Hz, 2H), 3.16 (S, 3H), δ (6.50–7.40 m-6H). Mass Spectrometry Calc'd: 193.1214, Found: 193.1224, m.p. 86°–88°.

EXAMPLE 4

1-Benzyl-1,3-dimethyl-2-hydroxyguanidine
R$^1$ = benzyl
R$^2$=R$^3$ = methyl

The procedure of Example 2 was employed to prepare 1-benzyl-1,3-dimethylhydroxyguanidine. An 11.14 g (0.0635 mol) amount of 1-benzyl-1,3-dimethylurea was contacted and reacted with phosgene as described. The 1-benzyl-1,3-dimethylhydroxyguanidine was isolated by the procedure of Example 2 to yield 5.1 g of 1-benzyl-1,3-dimethylhydroxyguanidine (42%) of the theoretical based on the urea employed.

EXAMPLE 5

1-Benzyl-1-methyl-3-ethyl-2-hydroxyguanidine
R$^1$ = benzyl
R$^2$ = methyl
R$^3$ = ethyl A 9.60 g (0.05 mol) portion of 1-benzyl-1-methyl-3-ethylurea was submitted to the synthesis sequence of Example 2. Isolation by the procedure of Example 2 yielded 5.85 g of 1-benzyl-1-methyl-3-ethylhydroxyguanidine.

Additional compounds that can be made by the procedures described include those of Table 1.

TABLE 1

| R¹ | R² | R³ |
|---|---|---|
| $C_6H_5$ | $C_2H_5$ | $C_2H_5$ |
| $C_6H_5CH_2$ | $C_2H_5$ | $C_2H_5$ |
| $C_6H_5CH_2CH_2$ | $CH_3$ | $CH_3$ |
| $C_6H_5CH_2CH_2$ | $CH_3$ | $C_2H_5$ |
| $C_6H_5CH_2CH_2$ | $C_2H_5$ | $CH_3$ |
| $C_6H_5CH_2CH_2$ | $C_2H_5$ | $C_2H_5$ |
| $3,4\text{-}Cl_2C_6H_3$ | $CH_3$ | $C_2H_5$ |
| $CH_3C_6H_4$ | $CH_3$ | $CH_3$ |
| $CH_3OC_6H_4$ | $CH_3$ | $CH_3$ |
| $FC_6H_4$ | $CH_3$ | $CH_3$ |
| $BrC_6H_4$ | $CH_3$ | $CH_3$ |
| $ClC_6H_4$ | $CH_3$ | $C_2H_5$ |
| $NO_2C_6H_4$ | $CH_3$ | $CH_3$ |
| $CF_3C_6H_4$ | $CH_3$ | $CH_3$ |
| $m\text{-}ClC_6H_4$ | $CH_3$ | $CH_3$ |
| $p\text{-}(CH_3)_2NSO_2C_6H_4$ | $C_2H_5$ | $C_2H_5$ |
| $CF_3SO_2C_6H_4$ | $CH_3$ | $CH_3$ |
| $CH_3SO_2C_6H_4$ | $CH_3$ | $CH_3$ |

As stated previously the compounds of the invention are useful in preparing 2-hydroxyguanidine 0-carbamates as shown in my parent application Ser. No. 373,147 filed June 25, 1973. The procedure in general involves making a solution of the 1,1,3-trisubstituted hydroxyguanidine in a suitable solvent such as methylene chloride, reacting it with an appropriate isocyanate, and recovering the 0-carbamate.

The 1,1,3-trisubstituted hydroxyguanidines of the invention chelate metal ions in aqueous solutions, and the chelate complexes can then be extracted by a solvent such as 1-butanol. The following is an example.

Aqueous solutions of cobaltous chloride and cupric acetate were prepared by dissolving 0.5 g in separate 5 ml portions of water. One ml of each solution was mixed with 1 ml of an aqueous methanol solution of 1,3-dimethyl-1-benzyl-2-hydroxyguanidine made by dissolving 0.2 g of the hydroxyguanidine in 5 ml methanol and 5 ml water. The addition was followed by an immediate color change. The cobalt went from red to pink and the copper from blue to green. Shaking the aqueous solutions with 2-3 ml of 1-butanol gave colored organic layers, indicative of extraction of the metal ion from the water.

When the experiment was repeated with a methanol solution of tetraisopropyl titanate, a bright yellow complex of titanium with the hydroxyguanidine was formed.

Chelating also occured when the above procedure was carried out with 1,3-diemthyl-1-phenyl-2-hydroxyguanidine.

The compounds of the invention are also useful as antidepressant agents in warm blooded animals. They can be employed in pharmaceutical compositions composed of the active ingredient, i.e., the compound(s) of the invention, in combination with non-toxic pharmaceutical carriers and additives. In any formulation of the antidepressant agent, the active ingredient will ordinarily be present in an amount from about 0.5% to 95% based on total weight of the composition.

Formulations include injectables and oral dosage forms such as tablets, hard and soft gelatin capsules, suspensions, syrups, elixirs and the like. Additives that can be employed in such formations include solvents and diluents, lubricants, binding agents, disintegrants, preservatives, colorants, flavors and other additives.

The compounds can be administered in a pharmaceutical carrier as treatment for psychiatric depressions of the reactive and endogenous types by any means that effects contact of the active ingredient compound with the site of action in the body of a warm blooded animal. For example, administration can be parenterally, i.e., subcutaneously, intravenously, intramuscularly or intraperitoneally. Alternatively or concurrently, administration can be by the oral route.

The dosage administered will be dependent upon the age, health and weight of the recipient, the type and severity of depression, kind of concurrent treatment, if any, frequency of treatment and the nature of the effect desired. Generally a daily dosage of active ingredient compound will be from about 0.01 to 50 mg/kg of body weight. Ordinarily, from 0.05 to 40 and preferably 0.1 to 10 mg/kg per day in one or more applications per day is effective to obtain desired results.

The antidepressant activity is evidenced by tests conducted in female white mice in which prevention of tetrabenazine-induced sedation and depression was demonstrated. This mouse test is predictive of human antidepressant response (Everett, G.M., "The Dopa Response Potentiation Test and Its Use In Screening for Antidepressant Drugs", pp. 164–167 in "Antidepressant Drugs", Proceeding of the First International Symposium, S. Garattini and M. N. G. Dukes, eds., 1967).

Groups of 10 Carworth $CF_1S$ female mice, 18–21 g each, were fasted 1.5 hours and were intubated with a hydroxyguanidine as antagonist to tetrabenazine at oral doses of 5, 25 and 125 mg/kg in 0.20 ml of 1% methyl cellulose (Methocel). Thirty minutes later the mice were challenged with tetrabenazine, 32 mg/kg intraperitoneally (dissolved in 0.20 ml of 0.05M KCl at pH 2.0). One hour after the hydroxyguanidine compound (30 minutes after tetrabenazine) the mice were examined for signs of exploratory activity and ptosis (eye-lid closure). Normal exploratory activity (relief from sedation) was recorded when a mouse lifted by the tail from a group of 10 in a testing box and placed on a stainless steel testing box lid (12.5 inches × 8 inches with 0.33 inch mesh) either turned its head horizontally 30° or moved to the edge of the screen within 10 seconds after being placed on the screen. Relief from ptosis was recorded when exactly 2 seconds after placing the mouse facing the observer, lid closure was less than 50% in both eyes.

With relief of ptosis as the criterion, the trisubstituted hydroxyguanidines prevent tetrabenazine-induced sedation in mice. The ptosis ED 50, i.e., the dose which blocked ptosis in 50% of the mice, is given below.

| Compound of Example | $ED_{50}$ (mg/kg) |
|---|---|
| 2 | < 0.3 |
| 3 | 2.7 |
| 4 | < 0.3 |
| 5 | 19 |

I claim:

1. A compound of the formula $$\begin{array}{c} R^1 \\ \diagdown \\ R^2 \diagup \end{array} N-\overset{\overset{\displaystyle NOH}{\|}}{C}-N \begin{array}{c} \diagup H \\ \diagdown R^3 \end{array} \quad \text{wherein}$$

$R^1$ is 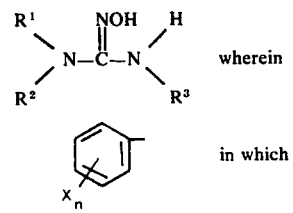 in which

X is F, Cl, Br, $C_1$–$C_3$ alkyl, $C_1$–$C_3$ alkoxy, $NO_2$, $CF_3$, $R^4R^5NCO$, $R^4R^5NSO_2$, or $R^6SO_2$;
$R^2$ and $R^3$ independently are methyl or ethyl;
$R^4$ and $R^5$ independently are H or $C_1$–$C_4$ alkyl;
$R^6$ is $CF_3$ or $C_1$–$C_4$ alkyl; and
$n$ is 0 to 2.

2. The compound of claim 1 wherein $R^1$ is phenyl.

3. The compound of claim 1 wherein $R^2$ and $R^3$ are each methyl.

4. The compound of claim 1 wherein one of $R^2$ and $R^3$ is ethyl.

5. The compound of claim 1 which is named 1-phenyl-1,3-dimethyl-2-hydroxyguanidine.

* * * * *